United States Patent
Levin et al.

(10) Patent No.: US 9,278,230 B2
(45) Date of Patent: Mar. 8, 2016

(54) ELECTRICAL SKIN REJUVENATION

(75) Inventors: Galit Levin, Nordiya (IL); Zev Sohn, Ginot Shomron (IL)

(73) Assignee: SYNERON MEDICAL LTD (IL)

( * ) Notice: Subject to any disclaimer, the term of this patent is extended or adjusted under 35 U.S.C. 154(b) by 916 days.

(21) Appl. No.: 13/203,436

(22) PCT Filed: Feb. 22, 2010

(86) PCT No.: PCT/IL2010/000149
§ 371 (c)(1),
(2), (4) Date: Oct. 19, 2011

(87) PCT Pub. No.: WO2010/097790
PCT Pub. Date: Sep. 2, 2010

(65) Prior Publication Data
US 2012/0041431 A1    Feb. 16, 2012

Related U.S. Application Data

(60) Provisional application No. 61/208,621, filed on Feb. 25, 2009.

(51) Int. Cl.
*A61N 1/40*     (2006.01)
*A61B 18/14*    (2006.01)
(Continued)

(52) U.S. Cl.
CPC . *A61N 1/40* (2013.01); *A61B 18/14* (2013.01); *A61B 2018/0047* (2013.01); *A61B 2018/00452* (2013.01); *A61B 2018/143* (2013.01); *A61N 1/328* (2013.01)

(58) Field of Classification Search
CPC ..... A61B 18/14; A61B 18/18; A61B 18/1492
USPC ................................ 606/20–52; 607/96–114
See application file for complete search history.

(56) References Cited

U.S. PATENT DOCUMENTS

| 1,430,354 A | 9/1922 | Burdick |
| 2,088,780 A | 8/1937 | Follese |

(Continued)

FOREIGN PATENT DOCUMENTS

| CA | 2495005 A1 | 2/2004 |
| CN | 1078383 A | 11/1993 |

(Continued)

OTHER PUBLICATIONS

Acne Clearance, LHE Clinical Casebook, Radiancy: Lighting the Future of Skin Care, © 2002.

(Continued)

*Primary Examiner* — Ronald Hupczey, Jr.
(74) *Attorney, Agent, or Firm* — Smith Risley Tempel Santos LLC; Gregory S. Smith (57) ABSTRACT

A method is provided for reducing a wrinkle on a skin surface (42). The method includes identifying a person having a skin surface (42) with a wrinkle and in response to identifying the person, positioning at respective sites on the skin surface (42) an array (44) of electrodes (60) coupled to an energy source (46). While the electrodes (60) are at the respective sites: during a first time period, applying energy from the energy source (46) to drive the electrodes (60) to apply radio frequency (RF) current at a first voltage, capable of ablating an epidermal layer of the skin; and during a second time period, applying energy from the energy source (46) to drive the electrodes (60) to apply current at a second voltage, lower than the first voltage. Other embodiments are also described.

10 Claims, 2 Drawing Sheets

(51) Int. Cl.
  *A61B 18/00* (2006.01)
  *A61N 1/32* (2006.01)

(56) References Cited

U.S. PATENT DOCUMENTS

| | | |
|---|---|---|
| 2,183,726 A | 2/1939 | Sommer et al. |
| 2,231,095 A | 2/1941 | Sommer et al. |
| 2,727,132 A | 12/1955 | Hills |
| 2,824,308 A | 2/1958 | Duncan |
| 2,888,927 A | 6/1959 | Fozard |
| 3,088,205 A | 5/1963 | Ellis |
| D196,532 S | 10/1963 | Facci |
| 4,016,886 A | 4/1977 | Doss et al. |
| 4,174,713 A | 11/1979 | Mehl |
| 4,182,329 A | 1/1980 | Smit et al. |
| 4,185,632 A | 1/1980 | Shaw |
| 4,200,104 A | 4/1980 | Harris |
| 4,211,230 A | 7/1980 | Woltosz |
| 4,228,931 A | 10/1980 | Ruscitti et al. |
| 4,321,926 A | 3/1982 | Roge |
| D269,294 S | 6/1983 | Rakocy et al. |
| D271,015 S | 10/1983 | Geraets |
| D271,199 S | 11/1983 | Geraets |
| 4,444,190 A | 4/1984 | Mutzhas |
| D274,462 S | 6/1984 | Rakocy et al. |
| 4,532,924 A | 8/1985 | Auth et al. |
| 4,550,728 A | 11/1985 | Runyon et al. |
| 4,553,936 A | 11/1985 | Wang |
| 4,566,454 A | 1/1986 | Mehl et al. |
| 4,686,986 A | 8/1987 | Fenyo et al. |
| 4,753,958 A | 6/1988 | Weinstein et al. |
| 4,784,135 A | 11/1988 | Blum et al. |
| 4,844,063 A | 7/1989 | Clark |
| 4,867,682 A | 9/1989 | Hammesfahr et al. |
| 4,869,584 A | 9/1989 | Dion |
| 5,016,999 A | 5/1991 | Williams |
| 5,071,418 A | 12/1991 | Rosenbaum |
| 5,125,928 A | 6/1992 | Parins et al. |
| 5,169,384 A | 12/1992 | Bosniak et al. |
| 5,286,479 A | 2/1994 | Garlich et al. |
| 5,316,473 A | 5/1994 | Hare |
| 5,319,363 A | 6/1994 | Welch et al. |
| 5,348,554 A | 9/1994 | Imran et al. |
| 5,353,798 A | 10/1994 | Sieben |
| 5,383,874 A | 1/1995 | Jackson et al. |
| 5,402,697 A | 4/1995 | Brooks |
| 5,406,340 A | 4/1995 | Hoff |
| 5,418,130 A | 5/1995 | Platz et al. |
| 5,449,378 A | 9/1995 | Schouenborg |
| 5,487,662 A | 1/1996 | Kipke et al. |
| 5,509,916 A | 4/1996 | Taylor |
| 5,520,684 A | 5/1996 | Imran |
| 5,521,392 A | 5/1996 | Kennedy et al. |
| 5,564,851 A | 10/1996 | Connely et al. |
| 5,582,476 A | 12/1996 | Hansen |
| 5,611,793 A | 3/1997 | Wilson et al. |
| 5,628,771 A | 5/1997 | Mizukawa et al. |
| 5,642,997 A | 7/1997 | Gregg et al. |
| 5,658,148 A | 8/1997 | Neuberger et al. |
| 5,674,267 A | 10/1997 | Mir et al. |
| 5,681,282 A | 10/1997 | Eggers et al. |
| 5,683,380 A | 11/1997 | Eckhouse et al. |
| 5,693,052 A | 12/1997 | Weaver |
| 5,698,866 A | 12/1997 | Doiron et al. |
| 5,704,935 A | 1/1998 | Pahl et al. |
| 5,707,403 A | 1/1998 | Grove et al. |
| 5,718,702 A | 2/1998 | Edwards |
| 5,722,411 A | 3/1998 | Suzuki et al. |
| 5,731,582 A | 3/1998 | West |
| 5,735,844 A | 4/1998 | Anderson et al. |
| 5,755,753 A | 5/1998 | Knowlton |
| 5,769,880 A | 6/1998 | Truckai et al. |
| 5,810,801 A | 9/1998 | Anderson et al. |
| 5,814,008 A | 9/1998 | Chen et al. |
| 5,824,023 A | 10/1998 | Anderson |
| 5,836,999 A | 11/1998 | Eckhouse et al. |
| 5,843,078 A * | 12/1998 | Sharkey .................. 606/41 |
| 5,843,143 A | 12/1998 | Whitehurst |
| 5,846,252 A | 12/1998 | Mehl, Sr. |
| 5,868,744 A | 2/1999 | Willmen |
| 5,871,469 A | 2/1999 | Eggers et al. |
| 5,871,524 A | 2/1999 | Knowlton |
| 5,873,855 A | 2/1999 | Eggers et al. |
| 5,888,198 A | 3/1999 | Eggers et al. |
| 5,919,219 A | 7/1999 | Knowlton |
| 5,935,143 A | 8/1999 | Hood |
| 5,949,514 A | 9/1999 | Wargon |
| 5,954,710 A | 9/1999 | Paolini et al. |
| 5,961,543 A | 10/1999 | Waldmann |
| 5,984,915 A | 11/1999 | Loeb et al. |
| 5,993,180 A | 11/1999 | Westerhof et al. |
| 6,024,733 A | 2/2000 | Eggers et al. |
| 6,030,384 A | 2/2000 | Nezhat |
| 6,053,172 A | 4/2000 | Hovda et al. |
| 6,056,548 A | 5/2000 | Neuberger et al. |
| 6,063,108 A | 5/2000 | Salansky et al. |
| 6,066,134 A | 5/2000 | Eggers et al. |
| 6,080,127 A | 6/2000 | Li et al. |
| 6,080,391 A | 6/2000 | Tsuchiya et al. |
| 6,081,934 A | 7/2000 | Stefanovsky et al. |
| 6,107,326 A | 8/2000 | Jori |
| 6,132,701 A | 10/2000 | Perez et al. |
| 6,148,232 A * | 11/2000 | Avrahami .................. 604/20 |
| 6,159,222 A | 12/2000 | Yiu |
| 6,186,960 B1 | 2/2001 | Tripp et al. |
| 6,187,001 B1 | 2/2001 | Azar et al. |
| 6,188,407 B1 | 2/2001 | Smith et al. |
| 6,190,609 B1 | 2/2001 | Chapman et al. |
| 6,191,110 B1 | 2/2001 | Jaynes et al. |
| 6,210,402 B1 | 4/2001 | Olsen et al. |
| 6,221,095 B1 | 4/2001 | Van Zuylen et al. |
| 6,228,078 B1 | 5/2001 | Eggers et al. |
| 6,231,571 B1 | 5/2001 | Ellman et al. |
| 6,231,593 B1 | 5/2001 | Meserol |
| 6,251,127 B1 | 6/2001 | Biel |
| 6,258,319 B1 | 7/2001 | Hearst et al. |
| 6,273,884 B1 | 8/2001 | Altshuler et al. |
| 6,277,116 B1 | 8/2001 | Utely et al. |
| 6,280,438 B1 | 8/2001 | Eckhouse et al. |
| 6,288,498 B1 | 9/2001 | Cheng |
| 6,308,413 B1 | 10/2001 | Westerhof et al. |
| 6,309,387 B1 * | 10/2001 | Eggers et al. ............... 606/41 |
| 6,311,090 B1 | 10/2001 | Knowlton |
| 6,325,797 B1 | 12/2001 | Stewart et al. |
| 6,343,400 B1 | 2/2002 | Massholder et al. |
| 6,343,933 B1 | 2/2002 | Montgomery et al. |
| 6,352,535 B1 | 3/2002 | Lewis et al. |
| 6,353,763 B1 | 3/2002 | George et al. |
| 6,360,116 B1 | 3/2002 | Jackson et al. |
| 6,381,497 B1 | 4/2002 | Knowlton |
| 6,405,090 B1 | 6/2002 | Knowlton |
| 6,406,157 B1 | 6/2002 | Audet |
| 6,413,255 B1 | 7/2002 | Stern |
| 6,413,268 B1 | 7/2002 | Hartman |
| 6,416,514 B1 | 7/2002 | Ein-Gal |
| 6,419,674 B1 | 7/2002 | Bowser et al. |
| 6,425,912 B1 | 7/2002 | Knowlton |
| 6,430,446 B1 | 8/2002 | Knowlton |
| 6,433,343 B1 | 8/2002 | Cimino et al. |
| 6,436,051 B1 | 8/2002 | Morris et al. |
| 6,438,424 B1 | 8/2002 | Knowlton |
| 6,440,121 B1 | 8/2002 | Weber et al. |
| 6,452,912 B1 | 9/2002 | Leem |
| 6,453,202 B1 | 9/2002 | Knowlton |
| 6,461,354 B1 * | 10/2002 | Olsen et al. ............... 606/41 |
| 6,461,378 B1 | 10/2002 | Knowlton |
| 6,461,567 B1 | 10/2002 | Hearst et al. |
| 6,462,070 B1 | 10/2002 | Hasan et al. |
| 6,470,216 B1 | 10/2002 | Knowlton |
| 6,471,716 B1 | 10/2002 | Pecukonis |
| 6,482,201 B1 | 11/2002 | Olsen et al. |
| 6,482,204 B1 | 11/2002 | Lax et al. |
| 6,487,447 B1 | 11/2002 | Weimann et al. |
| 6,493,940 B2 | 12/2002 | Westerhof et al. |

(56) References Cited

U.S. PATENT DOCUMENTS

| | | | |
|---|---|---|---|
| 6,494,900 B1 | 12/2002 | Salansky et al. |
| 6,497,702 B1 | 12/2002 | Bernaz |
| 6,508,813 B1 | 1/2003 | Althshuler |
| 6,511,475 B1 | 1/2003 | Altshuler et al. |
| 6,514,243 B1 | 2/2003 | Eckhouse et al. |
| 6,514,248 B1 | 2/2003 | Eggers et al. |
| 6,517,532 B1 | 2/2003 | Altshuler et al. |
| 6,533,775 B1 | 3/2003 | Rizoiu et al. |
| 6,544,259 B1 | 4/2003 | Tsaliovich |
| 6,544,261 B2 | 4/2003 | Ellsberry et al. |
| 6,558,653 B2 | 5/2003 | Andersen et al. |
| 6,572,637 B1 | 6/2003 | Yamazaki et al. |
| 6,582,429 B2 | 6/2003 | Krishnan et al. |
| 6,594,905 B2 | 7/2003 | Furst et al. |
| 6,595,990 B1 | 7/2003 | Weinstein et al. |
| 6,597,946 B2 | 7/2003 | Avrahami |
| 6,602,245 B1 | 8/2003 | Thiberg |
| 6,611,706 B2 | 8/2003 | Avrahami |
| 6,612,819 B1 | 9/2003 | Furst et al. |
| 6,618,620 B1 | 9/2003 | Freundlich et al. |
| 6,620,158 B2 | 9/2003 | Ronci |
| 6,629,974 B2 | 10/2003 | Penny et al. |
| 6,632,002 B1 | 10/2003 | Chubb et al. |
| 6,632,220 B1 | 10/2003 | Eggers et al. |
| 6,637,877 B1 | 10/2003 | Hartley et al. |
| 6,662,054 B2 | 12/2003 | Kreindel et al. |
| 6,663,620 B2 | 12/2003 | Altshuler et al. |
| 6,676,655 B2 | 1/2004 | McDaniel |
| 6,702,808 B1 | 3/2004 | Kreindel |
| 6,708,060 B1 * | 3/2004 | Avrahami et al. ............... 604/20 |
| 6,711,435 B2 | 3/2004 | Avrahami |
| 6,719,754 B2 | 4/2004 | Underwood et al. |
| 6,723,092 B2 | 4/2004 | Brown et al. |
| D490,156 S | 5/2004 | Fischer et al. |
| D490,526 S | 5/2004 | Jonsen |
| 6,740,079 B1 | 5/2004 | Eggers et al. |
| 6,743,211 B1 | 6/2004 | Prausnitz et al. |
| 6,749,626 B1 | 6/2004 | Bhat et al. |
| 6,758,845 B1 | 7/2004 | Weckwerth et al. |
| 6,761,729 B2 | 7/2004 | Babaev |
| 6,770,069 B1 | 8/2004 | Hobart et al. |
| 6,773,431 B2 | 8/2004 | Eggers et al. |
| 6,780,838 B2 | 8/2004 | Lipton et al. |
| 6,795,728 B2 | 9/2004 | Chornenky et al. |
| RE38,634 E | 10/2004 | Westerhof et al. |
| 6,887,260 B1 | 5/2005 | McDaniel |
| 6,889,090 B2 | 5/2005 | Kreindel |
| 6,893,435 B2 * | 5/2005 | Goble ........................ 606/41 |
| 6,905,496 B1 | 6/2005 | Ellman et al. |
| 6,918,907 B2 | 7/2005 | Kelly et al. |
| 6,974,450 B2 | 12/2005 | Weber et al. |
| 6,997,923 B2 | 2/2006 | Anderson et al. |
| 7,006,874 B2 | 2/2006 | Knowlton et al. |
| 7,013,179 B2 | 3/2006 | Carter et al. |
| 7,022,121 B2 | 4/2006 | Stern et al. |
| 7,077,840 B2 | 7/2006 | Altshuler et al. |
| 7,115,123 B2 | 10/2006 | Knowlton et al. |
| 7,115,124 B1 | 10/2006 | Xiao |
| 7,118,563 B2 | 10/2006 | Weckwerth et al. |
| 7,141,049 B2 | 11/2006 | Stern et al. |
| 7,153,298 B1 | 12/2006 | Cohen |
| 7,164,942 B2 | 1/2007 | Avrahami et al. |
| 7,204,832 B2 | 4/2007 | Altshuler et al. |
| 7,234,239 B2 | 6/2007 | Saito et al. |
| 7,238,183 B2 | 7/2007 | Kreindel |
| 7,266,414 B2 | 9/2007 | Cornelius et al. |
| 7,275,819 B2 | 10/2007 | Bleau |
| 7,278,991 B2 | 10/2007 | Morris et al. |
| 7,278,993 B2 | 10/2007 | Kelly et al. |
| 7,416,550 B2 | 8/2008 | Protsenko et al. |
| 7,435,247 B2 | 10/2008 | Woloszko et al. |
| 7,494,488 B2 | 2/2009 | Weber |
| 7,517,344 B2 | 4/2009 | Van Hal et al. |
| 7,601,149 B2 | 10/2009 | DiCarlo et al. |
| 7,713,266 B2 | 5/2010 | Elkins et al. |
| 7,771,419 B2 | 8/2010 | Carmel et al. |
| 7,824,394 B2 | 11/2010 | Manstein |
| 7,935,107 B2 | 5/2011 | Altshuler et al. |
| 7,963,985 B2 | 6/2011 | Minamoto et al. |
| 8,021,360 B2 | 9/2011 | Dunning et al. |
| 8,034,052 B2 | 10/2011 | Podhajsky |
| 8,109,927 B2 | 2/2012 | Kelly et al. |
| 8,128,622 B2 | 3/2012 | Podhajsky et al. |
| 8,133,216 B2 | 3/2012 | Knopp et al. |
| 8,135,475 B2 | 3/2012 | Kreindel et al. |
| 8,157,807 B2 | 4/2012 | Ferren et al. |
| 8,202,268 B1 | 6/2012 | Wells et al. |
| 8,206,381 B2 | 6/2012 | Lischinsky et al. |
| 8,216,215 B2 | 7/2012 | Flyash et al. |
| 8,235,989 B2 | 8/2012 | Palanker et al. |
| 8,292,882 B2 | 10/2012 | Danek et al. |
| 8,506,564 B2 | 8/2013 | Long et al. |
| 2001/0007068 A1 | 7/2001 | Ota et al. |
| 2002/0035363 A1 | 3/2002 | Edwards et al. |
| 2002/0058936 A1 | 5/2002 | Avrahami et al. |
| 2002/0104543 A1 | 8/2002 | Hollander et al. |
| 2002/0120256 A1 | 8/2002 | Furuno et al. |
| 2002/0120260 A1 | 8/2002 | Morris et al. |
| 2002/0120261 A1 | 8/2002 | Morris et al. |
| 2002/0128641 A1 | 9/2002 | Underwood et al. |
| 2002/0128648 A1 | 9/2002 | Weber et al. |
| 2002/0143373 A1 | 10/2002 | Courtnage et al. |
| 2002/0147384 A1 | 10/2002 | Uchikubo |
| 2002/0173780 A1 | 11/2002 | Altshuler et al. |
| 2002/0183245 A1 | 12/2002 | Hasan et al. |
| 2002/0190337 A1 | 12/2002 | House et al. |
| 2002/0198575 A1 | 12/2002 | Sullivan |
| 2003/0004499 A1 | 1/2003 | McDaniel |
| 2003/0032900 A1 | 2/2003 | Ella |
| 2003/0032950 A1 | 2/2003 | Altshuler et al. |
| 2003/0055413 A1 | 3/2003 | Altshuler et al. |
| 2003/0055414 A1 | 3/2003 | Altshuler et al. |
| 2003/0097162 A1 | 5/2003 | Kreindel |
| 2003/0109871 A1 | 6/2003 | Johnson et al. |
| 2003/0135250 A1 | 7/2003 | Lauman et al. |
| 2003/0139790 A1 | 7/2003 | Ingle et al. |
| 2003/0195494 A1 | 10/2003 | Altshuler et al. |
| 2003/0199863 A1 | 10/2003 | Swanson et al. |
| 2003/0199946 A1 | 10/2003 | Gutwein |
| 2003/0216719 A1 | 11/2003 | Debenedictis et al. |
| 2004/0010250 A1 | 1/2004 | Manna et al. |
| 2004/0010298 A1 | 1/2004 | Altshuler et al. |
| 2004/0015161 A1 | 1/2004 | Lovewell |
| 2004/0015162 A1 | 1/2004 | McGaffigan |
| 2004/0064167 A1 | 4/2004 | Berry et al. |
| 2004/0133251 A1 | 7/2004 | Altshuler et al. |
| 2004/0143308 A1 | 7/2004 | Lundahl et al. |
| 2004/0147984 A1 | 7/2004 | Altshuler et al. |
| 2004/0167501 A1 | 8/2004 | Island et al. |
| 2004/0181216 A1 | 9/2004 | Kelly et al. |
| 2004/0186466 A1 | 9/2004 | Chornenky |
| 2004/0193234 A1 | 9/2004 | Butler |
| 2004/0210214 A1 | 10/2004 | Knowlton |
| 2004/0236320 A1 | 11/2004 | Protsenko et al. |
| 2004/0260210 A1 | 12/2004 | Ella et al. |
| 2004/0267252 A1 | 12/2004 | Washington et al. |
| 2005/0015042 A1 | 1/2005 | Sun et al. |
| 2005/0033286 A1 | 2/2005 | Eggers et al. |
| 2005/0043653 A1 | 2/2005 | Trimmer et al. |
| 2005/0049543 A1 | 3/2005 | Anderson et al. |
| 2005/0075573 A1 | 4/2005 | Park et al. |
| 2005/0085804 A1 | 4/2005 | McGaffigan |
| 2005/0096646 A1 | 5/2005 | Wellman et al. |
| 2005/0137654 A1 | 6/2005 | Hoenig et al. |
| 2005/0137655 A1 | 6/2005 | MacFarland et al. |
| 2005/0143793 A1 | 6/2005 | Korman et al. |
| 2005/0147137 A1 | 7/2005 | Slatkine |
| 2005/0149012 A1 | 7/2005 | Penny et al. |
| 2005/0177139 A1 | 8/2005 | Yamazaki et al. |
| 2005/0288680 A1 | 12/2005 | Ingle et al. |
| 2006/0009763 A1 * | 1/2006 | Goble et al. ................ 606/49 |
| 2006/0036300 A1 | 2/2006 | Kreindel |
| 2006/0047281 A1 * | 3/2006 | Kreindel ................... 606/49 |
| 2006/0095096 A1 | 5/2006 | DeBenedictis et al. |

(56) References Cited

U.S. PATENT DOCUMENTS

| | | |
|---|---|---|
| 2006/0149343 A1 | 7/2006 | Altshuler et al. |
| 2006/0184024 A1 | 8/2006 | Da Silva et al. |
| 2006/0200213 A1 | 9/2006 | McDaniel |
| 2006/0206173 A1 | 9/2006 | Gertner et al. |
| 2006/0224217 A1 | 10/2006 | Burgmann et al. |
| 2006/0231568 A1 | 10/2006 | Lynn et al. |
| 2006/0247741 A1 | 11/2006 | Hsu et al. |
| 2006/0253112 A1 | 11/2006 | Suarez et al. |
| 2006/0259102 A1 | 11/2006 | Slatkine |
| 2006/0271028 A1 | 11/2006 | Altshuler et al. |
| 2007/0016117 A1 | 1/2007 | Sliwa et al. |
| 2007/0038206 A1 | 2/2007 | Altshuler et al. |
| 2007/0093798 A1 | 4/2007 | Debenedictis et al. |
| 2007/0106349 A1 | 5/2007 | Karni et al. |
| 2007/0129711 A1 | 6/2007 | Altshuler et al. |
| 2007/0129771 A1 | 6/2007 | Kurtz et al. |
| 2007/0142881 A1 | 6/2007 | Hennings |
| 2007/0191821 A1 | 8/2007 | Boxer Wachler |
| 2007/0191827 A1 | 8/2007 | Lischinsky et al. |
| 2007/0197895 A1 | 8/2007 | Nycz et al. |
| 2007/0198004 A1 | 8/2007 | Altshuler et al. |
| 2007/0206275 A1 | 9/2007 | Hemmer et al. |
| 2007/0213696 A1 | 9/2007 | Altshuler et al. |
| 2007/0239142 A1 | 10/2007 | Altshuler et al. |
| 2007/0239143 A1 | 10/2007 | Altshuler et al. |
| 2007/0239152 A1 | 10/2007 | Trezon |
| 2007/0264626 A1* | 11/2007 | DeBenedictis et al. ........... 435/4 |
| 2007/0271714 A1 | 11/2007 | Adam et al. |
| 2008/0051680 A1 | 2/2008 | Luebcke |
| 2008/0071334 A1 | 3/2008 | Hoenig et al. |
| 2008/0082090 A1 | 4/2008 | Manstein |
| 2008/0123238 A1 | 5/2008 | Campos et al. |
| 2008/0125658 A1 | 5/2008 | Lee et al. |
| 2008/0139901 A1 | 6/2008 | Altshuler et al. |
| 2008/0154247 A1 | 6/2008 | Dallarosa et al. |
| 2008/0183167 A1* | 7/2008 | Britva et al. ..................... 606/41 |
| 2008/0188846 A1 | 8/2008 | Palanker et al. |
| 2008/0200910 A1 | 8/2008 | Burger et al. |
| 2008/0214988 A1 | 9/2008 | Altshuler et al. |
| 2008/0215124 A1 | 9/2008 | Wagenaar et al. |
| 2008/0221504 A1 | 9/2008 | Aghion |
| 2008/0294153 A1 | 11/2008 | Allshuler et al. |
| 2008/0306476 A1 | 12/2008 | Hennings et al. |
| 2009/0036953 A1 | 2/2009 | Gustavsson |
| 2009/0043293 A1 | 2/2009 | Pankratov et al. |
| 2009/0054743 A1 | 2/2009 | Stewart |
| 2009/0105706 A1 | 4/2009 | Livneh |
| 2009/0112205 A1 | 4/2009 | McGill et al. |
| 2009/0119834 A1 | 5/2009 | Kneale et al. |
| 2009/0171341 A1 | 7/2009 | Pope et al. |
| 2009/0182315 A1 | 7/2009 | Zigan et al. |
| 2009/0192503 A1 | 7/2009 | Epshtein et al. |
| 2009/0222023 A1 | 9/2009 | Boone et al. |
| 2009/0234341 A1 | 9/2009 | Roth |
| 2009/0234342 A1 | 9/2009 | Ely et al. |
| 2009/0240310 A1 | 9/2009 | Kennedy |
| 2009/0299361 A1 | 12/2009 | Flyash et al. |
| 2010/0010480 A1 | 1/2010 | Mehta et al. |
| 2010/0063565 A1 | 3/2010 | Beerwerth et al. |
| 2010/0145321 A1 | 6/2010 | Altshuler et al. |
| 2010/0185193 A1 | 7/2010 | Kreindel |
| 2010/0185194 A1 | 7/2010 | Kreindel |
| 2010/0198134 A1 | 8/2010 | Eckhouse |
| 2010/0211055 A1 | 8/2010 | Eckhouse et al. |
| 2010/0249772 A1 | 9/2010 | Mehta et al. |
| 2010/0274329 A1 | 10/2010 | Bradley et al. |
| 2011/0112405 A1 | 5/2011 | Barthe et al. |
| 2011/0137386 A1 | 6/2011 | Kreindel |
| 2011/0166559 A1 | 7/2011 | Eckhouse et al. |
| 2011/0196363 A1 | 8/2011 | Kreindel |
| 2012/0016354 A9 | 1/2012 | Epshtein et al. |
| 2012/0022512 A1 | 1/2012 | Vaynberg |
| 2012/0022518 A1 | 1/2012 | Levinson |
| 2012/0123397 A1 | 5/2012 | Epshtein et al. |
| 2012/0143178 A9 | 6/2012 | Mehta |
| 2012/0143270 A1 | 6/2012 | Mehta |
| 2012/0197242 A1 | 8/2012 | Rosenberg |
| 2012/0290023 A1 | 11/2012 | Boyden et al. |
| 2013/0144280 A1 | 6/2013 | Eckhouse et al. |
| 2013/0289679 A1 | 10/2013 | Eckhouse et al. |

FOREIGN PATENT DOCUMENTS

| | | |
|---|---|---|
| EP | 0528055 A1 | 2/1993 |
| EP | 0569670 A2 | 11/1993 |
| EP | 0743029 B1 | 7/2002 |
| EP | 0824019 B1 | 11/2002 |
| EP | 1852060 A1 | 11/2007 |
| GB | 2125986 A | 8/1982 |
| GB | 2202442 A | 9/1988 |
| JP | 04299998 A2 | 10/1992 |
| JP | 06113920 A2 | 4/1994 |
| JP | 11132843 A2 | 12/1999 |
| JP | 2003034630 | 2/2003 |
| WO | WO-83/02389 A1 | 7/1983 |
| WO | WO-93/21992 A1 | 11/1993 |
| WO | WO-99/09143 A1 | 2/1999 |
| WO | WO-9909143 A1 | 2/1999 |
| WO | WO-99/34867 A1 | 7/1999 |
| WO | WO-02/078644 A2 | 10/2002 |
| WO | WO-02078644 A2 | 10/2002 |
| WO | WO-02094116 A1 | 11/2002 |
| WO | WO-03/039367 A1 | 5/2003 |
| WO | WO-03039367 A1 | 5/2003 |
| WO | WO-2006/128034 A1 | 11/2006 |

OTHER PUBLICATIONS

Acne Star web page, describing "How to use get rid of Acne Treatment", printed May 5, 2005.

Acne Star web page, describing Clinical Studies, "The Treatment of acne vulgaris with a novel device that uses Gallium—Nitride diode light", printed May 5, 2005.

Aesthetic Buyers Guide: The Leading Cosmetic Practice Resource, Jan./Feb. 2004, vol. 7, No. I.

Bollen, CM. et al., "Full- versus partial-mouth disinfection in the treatment of periodontal infections. A pilot study: long-tenn microbiological observations", J Clin Periodontol Oct. 1996;23(10):960-70 (Abstract).

Bollen, CM. et al., "Full- versus partial-mouth disinfection in the treatment of periodontal infections. A pilot study: long-term microbiological observations". J Clin Periodontol Oct. 1996;23(10):960-70 (Abstract).

Bollen, CM. et al., The effect of a one-stage full-mouth disinfection on different intra-0ral niches. Clinical and microbiological observations•. J Clin Periodontol Jan. 1998;25(1 ):56-66 (Abstract).

Bollen, CM. et al., "The effect of a one-stage full-mouth disinfection on different intra-oral niches. Clinical and microbiological observations", J Clin Periodontol Jan. 1998;25(1 ):56-66 (Abstract).

Calderhead, R. Glen, "The Photobiology of LED Phototherapy".

Calderl-Iead, R. Glen, "The Photobiology of LED Phototherapy".

Charakida et al., "Phototherapy in the Treatment of Acne Vulgaris, What is the Role?", Am. J. Clin. Dermatol 2004: 5(4): 211-216.

Cohen L.R., "What causes bad breath?", University of Toronto; webpage (printed before Nov. 2, 2004).

Cohen Lr., "What causes bad breath?", University of Toronto; webpage (printed before Nov. 2, 2004).

Coventry et al. (2000) "ABC of oral health: Periodontal disease" British Medical Journal, 321, 36-39.

De Soete, M. et al .. One-stage full-mouth disinfection. Long-term microbiological results analyzed by checker board DNA-DNA hybridization•, J Periodontol Mar. 2001; 72(3):374-82 (Abstract).

De Soete, M. et al., "One-stage full-mouth disinfection. Long-term microbiological results analyzed by checker board DNA-DNA hybridization", J Periodontol Mar. 2001; 72(3):374-82 (Abstract).

Elman M. et al., "The effective treatment of acne vulgaris by a high-intensity, narrow bank 405-420 nm light source", Cosmetic & Laser Ther 2003; 5: 111-116.

Elman M. et al., The effective treatment of acne vulgaris by a high-intensity, narrow bank 405-420 nm light source•, Cosmetic & Laser Ther 2003; 5: 111-116.

(56) References Cited

OTHER PUBLICATIONS

Flow Control Network web page, "Mini Diaphragm Pumps for Precision Dispensing" by Ping Lin, printed Aug. 2, 2005.
Friedberg J.S. et al., "Antibody-Targeted Photolysis Bacteriocidal Effects of Sn (IV) Chlorin e6-0extran-Monoclonal Antibody Conjugates", Annals New York Academy of Sciences 618:383-393, 1991.
Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.
Greenstein G., Full-mouth therapy versus individual quadrant root planning: a critical commentary, J Periodontol Jul. 2002;73(7):797-812 (Abstract).
Greenstein G., Full-mouth therapy versus individual quadrant root planning: a critical commentary, JPeriodontol Jul. 2002;73(7):797-812 (Abstract).
Guidelines for Limiting Exposure to Time-Varying Electric, Magnetic, and Magnetic Fields (Up to 300 GHz), International Commission on Non-Ionizing Radiation Protection, ICNIRP Guidelines, Apr. 1998, vol. 7 4, No. 4, pp. 494-522.
Hamblin, M. et al., "Rapid Control of Wound Infections by Targeted Photodynamic Therapy Monitored by In Vivo Bioluminescence Imagining", Photochemistry and Photobiology, 2002, 75(1 ): 51-57.
Hamblin, M. et al., Rapid Control of Wound Infections by Targeted Photodynamic Therapy Monitored by In Vivo Biluminescence Imagining•, Photochemistry and Photobiology, 2002, 75(1): 51-57.
Komerik et al. (2003) "In vivo killing of Porphyromonas gingivalis by toluidine blue-mediated photosensitization in an animal model" Antimicrobial Agents and Chemotherapy, 47(3), 932-940.
Krespi, et al. (2005) "Lethal photosensitization of oral pathogens via red-filtered halogen lamp" Oral Diseases, 11(S1), 92-95.
Krespi, et al. (2005) "Lethal photosensitization of oral pathogens via red-filtered halogen larnp" Oral Diseases, 11(S1 ), 92-95.
Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, May 1, 1990}__281-293.
Malik, Z. et al., "New Trends in Photobiology (Invited Review) Bactericidal Effects of Photoactivated Porphyrins • An Alternative Approach to Antimicrobial Drugs", Journal of Photochemistry and Photobiology, B: Biology, 5 J.19901__281-293.
Matevski D. et al., "Lethal photosensitization of periodontal pathogens by a red-filtered Xenon lamp in invitro", J. Periodont. Res. 2003; 38:428-435.
Matevski D. et al., "Lethal photosensitization of periodontal pathogens by a red-filtered Xenon lamp in invitro", JPeriodont. Res. 2003. 38:428-435.
Matevski D. et al., Sensitivity of Porphyromonas gingivalis to Light-Activated Toluidine Blue o•. University of Toronto, Faculty of Dentistry; Slide presentation (presented before Nov. 15, 2002).
Matevski D. et al., "Sensitivity of Porphyromonas gingivalis to Light-Activated Toluidine Blue O", University of Toronto, Faculty of Dentistry; Slide presentation (presented before Nov. 15, 2002).
Meisel et al. (2005) Photodynamic therapy for periodontal diseases: State of the are• J. Photochem. Photobiol., 79, 159-170.
Meisel etal. (2005) "Photodynamic therapy for periodontal diseases: State of the are" J. Photochem. Photobiol., 79, 159-170.
Mongardini, C. et al., One stage full- versus partial-mouth disinfection in the treatment of chronic adult or generalized ear 1 y-0nset periodontitis. I. Long-tenn clinical observations•, J Periodontol Jun. 1999;70(6):632-45 __[Abstrac!]__.
Mongardini, C. et al., "One stage full- versus partial-mouth disinfection in the treatment of chronic adult or generalized early-onset periodontitis. I. Long-term clinical observations", J Periodontol Jun. 1999;70(6):632-45 1Abstrac!2.__.
Morton C.A. et al., An open study to determine the efficacy of blue light in the treatment of mild to moderate acne: preliminary data (publication status unknown).
Nakano et al. (2002) "Correlation between oral malodor and periodontal bacteria" Microbes Infect., 4(6), 679-683.
Nakano et al. (2002) "Correlation between oral malodor and periodontal bacteria" Microbes Infect., 4(6). 679-683.
Ondine Biopharma web page—printed Oct. 15, 2002.
Papageorgiou et al., "Phototherapy with blue (415 nm) and red (660 nm) light in the treatment of acne vulgaris", British Journal of Dermatology 2000: 142: 973-978.
Pharmaceutical description, Levulan® Kerastick arninolevulinic acid I-IC!) for Topical Solution, 20'X.
Pharmaceutical description, Levulan® Kerastick •aminolevulinic acid HCI) for Topical Solution, 20%.
Quirynen, M. et al. Fuli- vs. partial-mouth disinfection in the treatment of periodontal infections: short-tennclinical and microbiological observations•. J Dent Res Aug. 1995;74(8):1459-67 (Abstract).
Quirynen, M. et al. "Full- vs. partial-mouth disinfection in the treatment of periodontal infections: short-term clinical and microbiological observations", J Dent Res Aug. 1995;74(8):1459-67 (Abstract).
Quirynen, M. et al., "One stage full- versus partial-mouth disinfection in the treatment of chronic adult or generalized ear 1 y-onset periodontitis. II. Long-term impact on microbial load", J Periodontol Jun. 1999;70(6):646-56 (Abstract).
Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).
Quirynen, M. et al., "The intra-oral translocation of periodontopathogens jeopardises the outcome of periodontal therapy", Journal of Clinical Periodontology, Jun. 2001, vol. 28, Issue 6, p. 499 (Abstract).
Quirynen, M. et al., The role of chlorhexidine in the one-stage full-mouth disinfection treatment of patients with advanced adults periodontitis. Long-term clinical and microbiological observations•. J Clin Periodontol 2000 A1.IQ;27.{fil:579-89 J__Abstrac!)__.
Quirynen, M. et al., "The role of chlorhexidine in the one-stage full-mouth disinfection treatment of patients with advanced adult periodontitis. Long-term clinical and microbiological observations", J Clin Periodontol 2000 A1!JL2~579-89 J__Abstrac__!).
Quirynen. M. et al., "One stage full- versus partial-mouth disinfection in the treatment of chronic adult or generalized early-onset periodontitis. II. Long-term impact on microbial load", J Peridontol Jun. 1999;70(6):646-56 J__Abstrac!2.__.
Sanz et al. (2001) "Fundamentals of breath malodour" Journal of Contemporary Dental Practice, 2(4 ), 1-13.
Sanz et al. (2001) "Fundamentals of breath malodour" Journal of Contemporary Dental Practice, 2(4), 1-13.
Sarkar et al. (1993) "Lethal photosensitization of bacteria in subgingival plaque from patients with chronic periodontitis" J. Periodont. Res , 28, 204-21 O.
Sarkar et al. (1993) "Lethal photosensitization of bacteria in subgingival plaque from patients with chronic periodontitis" J. Periodont. Res., 28, 204-210.
Search results from Delphion web site, dated Nov. 22, 2005.
Skin91 I .com web page regarding Peter Thomas Roth Clinical Acne Medication, acne treatment-Benzoyl Peroxide 5% pbp5, printed Aug. 19, 2005.
Skin91 I .corn web page regarding Peter Thomas Roth Clinical Acne Medication, acne treatment-Benzoyl Peroxide 5% pbp5, printed Apr. 19, 2005.
Soukos et al. (1998) "Targeted antimicrobial photochemotherapy", Antimicrobial Agents and Chemotherapy 42( 10 ), 2595-2601.
Soukos et al. (1998) "Targeted antimicrobial photochemotherapy", Antimicrobial Agents and Chemotherapy 42(10), 2595-2601.
Spire Awarded Contract for Ear Surgery Laser—Press Release Aug. 23, 2002.
Temperatures.com web page, "Thermistor Temperature Sensors," printed Aug. 2, 200.
Temperatures.corn web page, "Thermistor Temperature Sensors," printed Aug. 2, 200.
Vandekerckhove, BN. et al., "Full- versus partial-mouth disinfection in the treatment of periodontal infections. Long-term clinical observations of a pilot study", J Periodontol Dec. 1996;67(12):1251-9 (Abstract).

(56) References Cited

OTHER PUBLICATIONS

Vandekerckhove, BN. et al.. "Full- versus partial-mouth disinfection in the treatment of periodontal infections. Long-term clinical observations of a pilot study", J Periodontal Dec. 1996;67(12):1251-9 (Abstract).

Wainwright M., Photodynamic antimicrobial chemotherapy (PACT), Journal of Antimicrobial Chemotherapy (1998) 42, 13-28.

Wilson (2005) "Lethal photosensitisation of oral bacteria and its potential application in the photodynamic therapy of oral infection" Photochem. Photobiol. Sci . . . 3, 412-418.

Wilson (2005) "Lethal photosensitisation of oral bacteria and its potential application in the photodynamic therapy of oral infection" Photochem. Photobiol. Sci., 3, 412-418.

Wilson et al. (1995) "Bacteria in supragingival plaque samples can be killed by low-power laser light in the presence of a photosensitizer" J. Appl. Bacteriol . . . 78, 569-574.

Wilson et al. (1995) "Bacteria in supragingival plaque samples can be killed by low-power laser light in the presence of a photsensitizer" J. Appl. Bacteriol., 78, 569-574.

Wood, et al. (1999) "An in vitro study of the use of photodynamic therapy for the treatment of natural oral plaque biofilms formed in vivo" J. Photochem. Photogiol. B: Biol . . . 50, 1-7.

Wood, et al. (1999) "An in vitro study of the use of photodynamic therapy for the treatment of natural oral plaque biofilrns formed in vivo" J. Photochem. Photogiol. B: Biol., 50, 1-7.

www.lightbioscience.com web page, Gentle Waves Cosmcceuticals, printed Jul. 29, 200.

www.lightbioscience.com web page, Gentle Waves LED Photomodulation Fact Sheet, printed Jul. 29, 2005.

www.lightbioscience.com web page, GentleWaves Cosmeceuticals, printed Jul. 29, 200.

www.lightbioscience.com web page, GentleWaves LED Photomodulation Fact Sheet, printed Jul. 29, 2005.

Guidelines for Limiting Exposure to Time-Varying Electric, Magnetic, and Electromagnetic Fields (Up to 300 GHz), International Commission on Non-Ionizing Radiation Protection, ICNIRP Guidelines, Apr. 1998, vol. 74, No. 4, pp. 496-522.

PCT/IL11/00256 International Search Report.
PCT/IL11/00170 International Search Report.
PCT/IL10/00751 International Search Report.
PCT/IL10/00557 International Search Report.
PCT/IL10/00173 International Search Report.
PCT/IL09/00693 International Search Report.
PCT/IL09/00033 International Search Report.

* cited by examiner

ELECTRICAL SKIN REJUVENATION

CROSS-REFERENCES TO RELATED APPLICATIONS

The present application claims the priority of U.S. Provisional Application 61/208,621 to Levin, entitled, "Electrical skin rejuvenation," filed Feb. 25, 2009, which is incorporated herein by reference.

FIELD OF EMBODIMENTS OF THE INVENTION

Some embodiments of the present invention relate generally to skin rejuvenation, and particularly to methods and apparatus for wrinkle reduction.

BACKGROUND

Skin, the body's largest organ, is composed of multiple layers. The outer layer, epidermis, is divided into several sublayers; the outermost layer is termed stratum corneum epidermidis. The stratum corneum is generally a non-innervated cell layer consisting of mainly large, dead cells that lack nuclei. Beneath the epidermis, lies the dermis skin layer, which is tightly connected to the epidermis.

A major structural component of the skin is collagen, a fibrous protein, which contributes to skin strength and elasticity. As such, collagen formation and remodeling lead to changes in mechanical properties of the skin such as texture and resilience. Typically, collagen plays an important role in the regeneration of epidermal tissue in wounded skin. Collagen is produced during the wound healing process, thus increasing the tensile strength of a wound.

Collagen contraction, or thermal shrinkage of collagen, occurs by the dissociation of heat-sensitive bonds of the collagen molecule. Thermal denaturing of collagen results in a tightening effect of the skin. In contrast, age-related degradation of collagen leads to sagging of the skin and the formation of wrinkles. Many wrinkles appear on exposed areas of the skin, e.g., the face, the neck and the forearms. These visible effects of aging of the skin are disturbing to some individuals, and therefore methods for rejuvenation of maturing or damaged skin are of interest.

U.S. Pat. No. 6,461,354 to Olsen et al. describes systems and methods for selectively applying electrical energy to a target location on an external body surface, such as for skin tissue removal and/or collagen shrinkage in the epidermis or dermis, e.g., the removal of pigmentations, vascular lesions (e.g., leg veins), scars, tattoos, etc., and for other surgical procedures on the skin, such as tissue rejuvenation, cosmetic surgery, wrinkle removal, hair removal and/or transplant procedures. The described system and methods apply high frequency (RF) electrical energy to one or more electrode terminals adjacent an external body surface, such as the outer surface of the skin, to remove and/or modify the structure of tissue structures within the skin. Depending on the specific cosmetic procedure, the described system and methods may be used to: (1) volumetrically remove tissue or hair (i.e., ablate or effect molecular dissociation of the tissue structure); (2) separate a tissue layer from an underlying tissue layer so that the tissue layer can be removed; (3) shrink or contract collagen connective tissue; and/or (4) coagulate blood vessels underlying the surface of the skin.

U.S. Pat. No. 6,381,498 to Knowlton describes a method and apparatus that applies radiant energy through the skin to underlying collagen tissue, and is described as not substantially modifying melanocytes and other epithelial cells in the epidermis. A membrane is adapted to receive an electrolytic solution and become inflated to substantially conform to a contacting exterior surface of the membrane to a skin layer. The membrane includes a cooling lumen for receiving cooling fluid. One or more thermal electrodes positioned in the membrane transfers thermal energy to the electrolytic solution. The electrolytic solution and cooling fluid is described as creating a reverse thermal gradient from the skin surface to the underlying collagen tissue. A thermal power source is coupled to the thermal electrodes, and a source of electrolytic solution is coupled to the membrane.

US 2006/0036300 to Kreindel describes a method of lipolysis. The method comprises deforming a region of skin so that the region of skin protrudes from surrounding skin. One or more radio frequency (RF) electrodes are positioned on the protruding region of skin so as to generate an electrical current through adipose tissue in the protruding region of skin when a voltage is applied to the electrode or electrodes. A voltage is then applied to the electrode or electrodes so as to deliver sufficient RF energy to the protruding region of skin to damage subcutaneous adipose tissue. The described method may be used, for example, to achieve a reduction in body weight, cellulite reduction, loose skin reduction, wrinkle treatment, body surface tightening, skin tightening, and collagen remodeling.

U.S. Pat. No. 6,684,107 to Binder describes a system for reducing wrinkles on human skin that utilizes an electrode to conduct a microcurrent through the surface of the wrinkle into the underlying dermal layer. The electrode is moved in multiple passes along the length of the wrinkle, with the electrode in contact with the surface of the wrinkle while generating a periodically repeating microcurrent having a peak amplitude in the range of 10-40 microamps, a peak current density in the range of 10-50 microamps/cm.sup.2, and a frequency in the range of 5-15 Hz. The electrode device is described as self-contained in a battery-containing, cordless case from which a contact electrode protrudes. A hand-engaging second electrode on the surface of the case completes a conductive path through the user's body.

U.S. Pat. No. 6,148,232 to Avrahami describes a device for ablating the stratum corneum epidermidis of a subject, including a plurality of electrodes, which are applied to the subject's skin at respective points. A power source applies electrical energy between two or more of the plurality of electrodes, in order to cause ablation of the stratum corneum primarily in an area intermediate the respective points.

U.S. Pat. No. 6,611,706 to Avrahami describes a device for facilitating transdermal passage of a substance through skin on the body of a subject. The device preferably includes an electrode and a control unit. In a preferred embodiment, the control unit is adapted to drive the electrode to apply to the skin a current capable of ablating stratum corneum epidermidis of the skin, so as to facilitate transdermal passage of the substance. The control unit detects generation of at least one spark responsive to application of the current, and modifies a parameter of the current responsive to detecting the generation of the at least one spark.

U.S. Pat. No. 6,708,060 to Avrahami describes a device for treating skin on the body of a subject. The device includes a plurality of electrodes, which are adapted to be placed in contact with the skin and then moved across the skin while maintaining electrical contact with the skin. The device additionally includes a power source, which is adapted to apply a current between two or more of the plurality of electrodes at the same time as the electrodes are being moved across the skin.

Reliant Technologies (California, US) distributes the Fraxel family of cosmetic products, which includes three fractional lasers that produce two non-ablative treatments and one ablative treatment.

The following patent and patent applications may be of interest:

US 2005/0003518 to Avrahami et al.
US 2005/0119605 to Sohn
US 2005/0187497 to Nguyen
US 2006/0089688 to Panescu
US 2007/0270732 to Levine
US 2007/0287949 to Levine et al.
US 2007/0292445 to Levine
US 2008/0114281 to Birchall et al.
U.S. Pat. No. 5,569,242 to Lax et al.
U.S. Pat. No. 5,746,746 to Garito et al
U.S. Pat. No. 6,026,327 to Dervieux
U.S. Pat. No. 6,597,946 to Avrahami et al.
U.S. Pat. No. 6,711,435 to Avrahami
U.S. Pat. No. 7,123,957 to Avrahami
U.S. Pat. No. 7,335,377 to Stern
U.S. Pat. No. 7,395,111 to Levine et al.

---

US 2002/0068930
US 2002/0087155
US 2002/0095152
US 2002/0128641
US 2002/0193789
US 2003/0009164
US 2003/0097126
US 2003/0097129
US 2003/0097162
US 2003/0120269
US 2003/0130655
US 2003/0158545
US 2003/0163178
US 2003/0187488
US 2003/0212396
US 2004/0215184
US 2005/0107832
US 2005/0256519
US 2006/0036300
US 2006/0047281
US 2006/0058727
US 2006/0173518
US 2007/0010811
US 2007/0032840
U.S. Pat. No. 5,660,836
U.S. Pat. No. 5,681,282
U.S. Pat. No. 5,697,909
U.S. Pat. No. 5,746,746
U.S. Pat. No. 5,755,753
U.S. Pat. No. 5,766,153
U.S. Pat. No. 5,843,019
U.S. Pat. No. 5,888,198
U.S. Pat. No. 5,919,219
U.S. Pat. No. 5,948,011
U.S. Pat. No. 6,119,038
U.S. Pat. No. 6,179,836
U.S. Pat. No. 6,235,020
U.S. Pat. No. 6,241,753
U.S. Pat. No. 6,264,652
U.S. Pat. No. 6,355,032
U.S. Pat. No. 6,377,855
U.S. Pat. No. 6,381,498
U.S. Pat. No. 6,387,380
U.S. Pat. No. 6,405,090
U.S. Pat. No. 6,413,255
U.S. Pat. No. 6,432,103
U.S. Pat. No. 6,461,354
U.S. Pat. No. 6,468,270
U.S. Pat. No. 6,482,201
U.S. Pat. No. 6,544,261
U.S. Pat. No. 6,557,559
U.S. Pat. No. 6,575,968

-continued

U.S. Pat. No. 6,623,454
U.S. Pat. No. 6,632,193
U.S. Pat. No. 6,662,054
U.S. Pat. No. 6,684,107
U.S. Pat. No. 6,766,202
U.S. Pat. No. 6,832,996
U.S. Pat. No. 6,837,887
U.S. Pat. No. 6,837,888
U.S. Pat. No. 6,896,672
U.S. Pat. No. 6,974,453
U.S. Pat. No. 7,006,874
U.S. Pat. No. 7,010,343
U.S. Pat. No. 7,022,121
U.S. Pat. No. 7,083,580
U.S. Pat. No. 7,115,123
U.S. Pat. No. 7,141,049
U.S. Pat. No. 7,189,230
U.S. Pat. No. 7,201,750
WO 9426228
WO 9632051
WO 9634568
WO 9803220
WO 9917690
WO 9920185
WO 9920213
WO 9926546
WO 0009053
WO 0053113
WO 0056229
WO 0062685
WO 0062698
WO 0195819
WO 0160273
WO 02102255
WO 03005882
WO 03028540
WO 03043696
WO 03065915
WO 03079916
WO 03086217
WO 04086943
WO 04089185
WO 04105861
WO 06054150
WO 06080012
WO 06109334

---

SUMMARY

In some applications of the present invention, an apparatus and a method for reducing a wrinkle on a skin surface is provided. An array of electrodes coupled to an energy source is positioned on the wrinkle. The electrodes remain at the same sites on the skin surface for at least two successive periods of time. During the first period of time, energy from the energy source is applied to drive the electrodes to apply radio frequency (RF) current at a first voltage. The current applied at the first voltage is capable of locally ablating the epidermal tissue (and typically superficial dermal tissue) in close proximity to the electrodes. Ablation of the epidermal tissue (and typically superficial dermal tissue) by the applied RF current generates micro-channels through the epidermis (and typically superficial dermis). The formation of the micro-channels induces natural body fluid to enter the micro-channels. Whereas during ablation the resistance between electrodes increases, the resistance subsequently decreases when body fluid enters the micro-channels. During the subsequent, second time period, energy from the energy source is applied to drive the electrodes to apply current at a second voltage, lower than the first voltage. The current applied at the second voltage is sufficient to continuously heat the fluid within the micro-channels and underlying tissue, but generally does not cause further ablation.

The inventors hypothesize that the ablation of epidermal tissue (and typically superficial dermal tissue) with subsequent heating of underlying tissue leads to collagen regeneration and remodeling, resulting in skin rejuvenation. The first phase of RF application ablates micro-channels in the epidermal layer (and typically superficial dermal layer) of the skin in close proximity to the electrodes, as described hereinabove. The ablation of the micro-channels triggers the initiation of a wound healing process in the skin, in which production of collagen is induced. The second phase of lower voltage, non-ablating current application heats the natural body fluid present within the micro-channels, leading to the controlled heating of underlying collagen tissue, causing thermally-mediated collagen contraction. The effect of the combined ablation and heating method of these applications of the present invention is skin tightening and wrinkle reduction. It is noted that although a wound healing process is initiated, ablation of micro-channels into the epidermis (and typically superficial dermis), as provided herein, generally does not cause pain to a subject.

The term "micro-channel," as used in the context of the present patent application and in the claims, refers to a pathway generally extending from the surface of the skin through at least the epidermis. Such micro-channels are formed due to local power dissipation leading to ablation of the epidermis (and typically superficial dermis) when an electric field of sufficient magnitude is applied to a small area of the skin, in contact with the electrodes, for a sufficient period of time.

There is therefore provided, in accordance with some applications of the invention, a method for reducing a wrinkle on a skin surface, including:

identifying a person having a skin surface with a wrinkle;

in response to identifying the person, positioning at respective sites on the skin surface an array of electrodes coupled to an energy source; and while the electrodes are at the respective sites:

during a first time period, applying energy from the energy source to drive the electrodes to apply radio frequency (RF) current at a first voltage, capable of ablating an epidermal layer of the skin; and during a second time period, applying energy from the energy source to drive the electrodes to apply current at a second voltage, lower than the first voltage.

In some applications, applying energy during the first time period includes applying the energy for 1-20 ms.

In some applications, applying energy during the second time period includes applying the energy for at least 1 second.

In some applications, applying energy during the second time period includes initiating applying the energy through a given electrode during the second time period at least 10 ms after application of energy through the given electrode during the first time period.

In some applications, applying energy during the second time period includes applying only non-ablating energy during the second time period.

In some applications, applying energy during the first time period includes setting a voltage of the energy applied during the first time period to be 150-350 V base-to-peak.

In some applications, applying energy during the second time period includes setting a voltage of the energy applied during the second time period to be 10-200 V base-to-peak.

In some applications, applying energy during the second time period includes setting a voltage of the energy applied during the second time period to be 10-100 V base-to-peak.

In some applications, applying energy during the first time period includes setting a frequency of the energy applied during the first time period to be 50-500 kHz.

In some applications, applying energy during the second time period includes setting a frequency of the energy applied during the second time period to be 50-500 kHz.

In some applications, applying energy during the first time period includes ablating micro-channels in the epidermal layer.

In some applications, applying energy during the second time period includes initiating application of the energy during the second time period subsequently to filling of the micro-channels with body fluid.

There is further provided, in accordance with some applications of the present invention, apparatus for reducing a wrinkle on a skin surface, including:

an array of electrodes configured to be placed on the skin surface; and an energy source coupled to the array of electrodes and configured to apply energy to drive the electrodes to apply ablating current at a first voltage during a first period of time and to apply non-ablating current at a second voltage, lower than the first voltage, during a second period of time.

In some applications, the energy source is configured to apply energy for 1-20 ms during the first time period.

In some applications, the energy source is configured to apply energy for at least 1 second during the second time period.

In some applications, the energy source is configured to apply energy, during the second time period, through a given electrode at least 10 ms after application of energy through the given electrode during the first time period.

In some applications, the energy source is configured to convey to the electrodes 150-350 V base-to-peak during the first period of time.

In some applications, the energy source is configured to convey to the electrodes 10-200 V base-to-peak during the second period of time.

In some applications, the energy source is configured to convey to the electrodes 10-100 V base-to-peak during the second period of time.

In some applications, the energy source is configured to apply energy at a frequency of 50-500 kHz during the first time period.

In some applications, the energy source is configured to apply energy at a frequency of 50-500 kHz during the second time period.

In some applications, the array of electrodes includes at least 10 electrodes.

In some applications, the array of electrodes includes at least 50 electrodes.

In some applications, the electrodes of the array are arranged in a 2×n rectangular array.

In some applications, the array of electrodes includes electrodes, each electrode 60-80 um in diameter.

In some applications, the array of electrodes includes electrodes, each electrode 50-400 um in length.

In some applications, the array of electrodes includes electrodes, each electrode 100-250 um in length.

In some applications, the array of electrodes includes electrodes generally evenly spaced in the array, the distance between adjacent electrodes being 0.5-1.5 mm.

In some applications, the energy source is configured to apply energy capable of ablating micro-channels in an epidermal layer of the skin during the first period of time.

In some applications, the energy source is configured to initiate application of energy subsequently to filling of the micro-channels with body fluid, during the second period of time.

There is yet further provided, in accordance with some applications of the present invention, apparatus for reducing a wrinkle on a skin surface, including:

an array of at least 10 electrodes, each electrode at least 150 um in length, configured to be placed on the skin surface; and an energy source coupled to the array of electrodes and configured to apply energy to drive the electrodes to apply 50-500 kHz current capable of ablating an epidermis layer of the skin.

In some applications, the array includes at least 100 electrodes.

In some applications, the electrodes of the array are arranged in a 2×n rectangular array.

In some applications, the electrodes of the array are arranged in an m×n rectangular array, n being at least four times greater than m.

In some applications, each electrode is 60-80 um in diameter.

In some applications, the array of electrodes includes electrodes generally evenly spaced in the array, the distance between adjacent electrodes being 0.5-1.5 mm.

There is also provided, in accordance with some applications of the present invention, a method for reducing a wrinkle on a skin surface, including:

identifying a person having a skin surface with a wrinkle;

in response to identifying the person, positioning at respective sites on the skin surface at least 10 electrodes coupled to an energy source; and ablating an epidermal layer of the skin by applying energy from the energy source to drive the electrodes to apply 50-500 kHz current.

The present invention will be more fully understood from the following detailed description of embodiments thereof, taken together with the drawings, in which:

DETAILED DESCRIPTION OF THE EMBODIMENTS

Figure 1A:
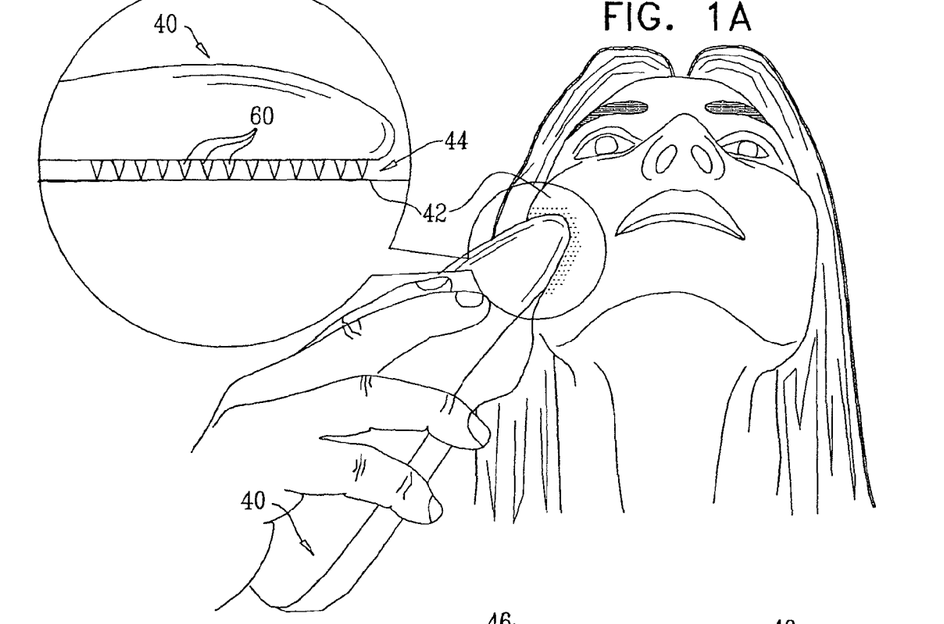
FIG. 1A is a schematic illustration of apparatus for reducing wrinkles positioned on a skin surface containing a wrinkle, in accordance with some applications of the present invention.

FIG. 1A is a schematic illustration of apparatus 40 for reducing wrinkles, during use by a subject, in accordance with some applications of the present invention. Apparatus 40 is positioned on skin surface 42 containing a wrinkle (e.g., on the face, the forehead or the neck). Apparatus 40 typically comprises an energy source 46, a reusable control unit 48, and a typically disposable sterile array 44 of electrodes 60. When positioned on skin surface 42, array 44 of electrodes 60 is in direct contact with the stratum corneum layer of the skin.

Array 44 is typically 0.5-2 cm2 (e.g., 0.96 cm2), and typically comprises 10-1000 electrodes, e.g., 50-250 electrodes.

In all experiments described herein, array 44 comprises 144 electrodes. For some applications (e.g., those used in the experiments described herein), array 44 is arranged as an n×n array, i.e., a square array of electrodes. For other applications, e.g., where it is desired to primarily apply energy in a series of applications along the length of a wrinkle (and to a lesser extent to surrounding tissue), a long, thin, rectangular array is utilized, e.g., an m×n array, where m is typically 2, 3, 4, 5, or 6, and n is typically between 10 and 30, or between 30 and 100. For example, the array may be a 2×10 array. For these applications, n is typically at least four times greater than m (e.g., at least eight times greater than m).

Each electrode 60 is typically 60 um-80 um in diameter and 50 um-400 um in length, e.g., 100-250 um in length, in order to reach the epidermal tissue (and typically superficial dermal tissue). Array 44 is typically snapped on to a housing of apparatus 40 prior to use and ejected after use.

The distance between adjacent electrodes is typically 0.5-1.5 mm, and the electrodes are typically generally evenly spaced in the array. With an array of small diameter electrodes, which are typically generally evenly-spaced electrodes, and with no particular effort by the operator of the apparatus, generally uniform heating of the skin under array 44 is obtained, particularly during the second time period of energy application (described hereinbelow).

Control unit 48 (FIGS. 1B-C) comprises electronic and software components configured to drive energy source 46 to initiate or discontinue energy application to electrodes 60.

Figure 1B:
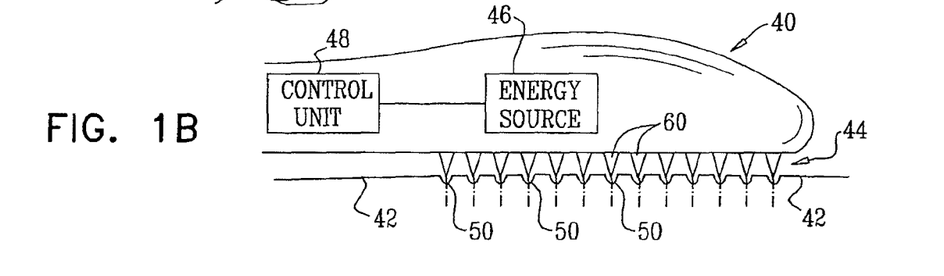
FIG. 1B is a schematic illustration of an array of electrodes positioned in contact with the skin surface, and respective ablated sites on the subject's skin, in accordance with some applications of the present invention.

Reference is made to FIG. 1B, which is a schematic illustration of array 44 positioned in contact with skin surface 42, in accordance with some applications of the present invention. In some applications of the present invention, array 44 remains at the same sites on skin surface 42 for at least two periods of time. Energy source 46 applies energy to drive array 44 of electrodes 60 to apply RF energy to skin surface 42. Energy source 46 is configured to apply energy to drive the electrodes to apply current at different voltages during the two time periods. During the first time period, represented in FIG. 1B, energy source 46 applies energy to drive array 44 of electrodes to apply a 1-20 ms burst of RF current at 200-350 V base-to-peak (i.e., 400-700 V peak-to-peak) and 50-500 kHz (e.g., 100 kHz) to the epidermis (and typically superficial dermis) of skin surface 42.

When apparatus 40 drives a sufficient amount of energy through the epidermis (and typically superficial dermis), during the first time period, these skin layers are ablated by the energy dissipating through them. Each individual electrode typically applies this current at a current of 1-20 mA. Typically, 2-12 electrodes (e.g., four electrodes) are simultaneously driven to drive the RF current into the skin, resulting in a correspondingly higher total instantaneous current (e.g., 4-80 mA). The remaining electrodes in array 44 typically serve as return electrodes, and due to their greater number, the return electrodes produce substantially lower current densities in the skin. This ablation creates micro-channels 50, i.e. physical pores in the epidermis (and typically superficial dermis). Micro-channels 50 are accurately reproducible as well as typically small and not visible to a naked eye. Depending on local skin conditions and the current protocol used, the micro-channels are typically 40-100 um in diameter, and 50-400 um (e.g., 30-200 um) in depth.

When each micro-channel 50 has formed in response to current flow by the electrodes, it remains an empty pore until body fluid permeates it. Typically, a given micro-channel 50 is filled by natural body fluid within approximately 30 ms after formation of the micro-channel has occurred. Ablation of micro-channels 50 generally does not cause pain or substantial trauma to skin layers underlying the superficial dermis. Although any wound caused by ablation of the skin is minimal, a natural process of wound healing is induced by formation of micro-channels 50. Production of collagen, which occurs naturally as part of wound healing, leads to a smoother, elastic skin appearance.

Figure 1C:
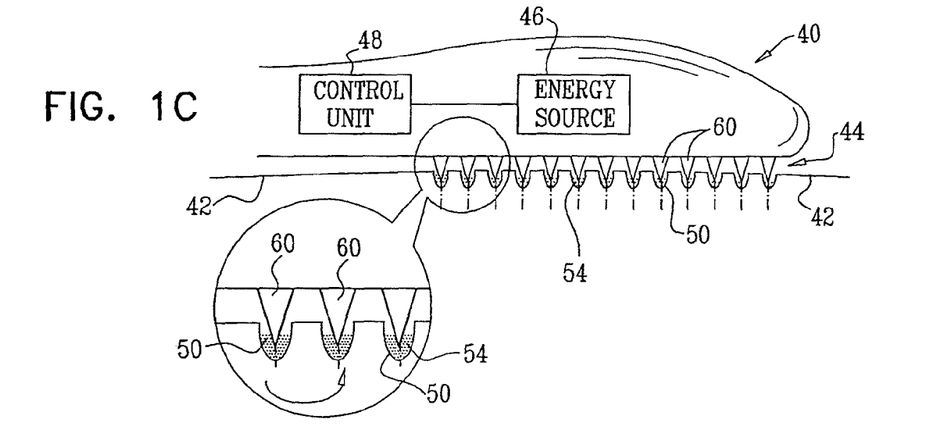
FIG. 1C is a schematic illustration of the array of electrodes positioned in contact with the skin surface, during a subsequent heating step, in accordance with some applications of the present invention.

Reference is made to FIG. 1C, which is a schematic illustration of array 44 positioned in contact with skin surface 42, without having been moved from the site where ablation was produced, in accordance with some applications of the present invention. As described hereinabove, energy source 46 drives electrodes 60 to apply current at different voltages during two time periods. FIG. 1C represents the second time period, in which energy source 46 applies energy to drive the electrodes to apply current at a lower voltage than was applied during the first time period. Although the current applied by the electrodes during the second time period can be AC or DC and can have a range of parameters that would induce heating, the current typically has a frequency of 50-500 kHz (e.g., 100 kHz), and may, for example, have the same frequency as that applied during the first time period.

In accordance with a protocol for the first and second time periods, ablation through a given electrode, or small group of electrodes (e.g., four electrodes) is performed during the first time period for that subset of one or more electrodes. Then, another subset of one or more electrodes ablates, during a first time period for that subset of electrodes. This process is repeated until typically substantially all of the electrodes have applied ablating energy to the skin. Subsequently, in the second time period, current is applied at a lower voltage through all of the electrodes, in order to induce uniform heating across the area of skin under array 44. The current driven by energy source 46 during the second time period is typically (but not necessarily) less than 100 mA, and is usually about 10-50 mA. The current driven through any one electrode during the second time period is typically 0.1-1 mA. For some applications, e.g., when array 44 has a smaller number of electrodes, or not all of the electrodes are applying current simultaneously, the current driven through any one electrode may be 1-10 mA.

In some applications, the second period of time is initiated on an electrode-by-electrode basis or a subset-by-subset basis, typically at least 10 ms from the termination of the first time period at any given electrode. For example, each electrode, or small subset of electrodes, may have its own first and second time periods, before another electrode or subset of electrodes has its first time period. For some applications, a first subset of one or more of the electrodes are applying energy in accordance with a first time period protocol, while another subset of one or more electrodes are applying energy in accordance with a second time period protocol.

Typically, in at least one operational mode of apparatus 40, the number n2 of electrodes applying non-ablating energy during any given second time period is higher than the number n1 of electrodes that apply ablating energy during any given first time period. For example, n2 is typically at least 3 or 10 times higher than n1.

The duration of current application during the second time period is typically 1-30 seconds, or 30-200 seconds. The energy applied during the second time period is non-ablating, but typically sufficient to heat body fluid 54 present within micro-channels 50 to a temperature suitable for inducing ongoing changes to collagen. In an experiment, an array 44 of 144 electrodes, 70 um in length, applied 100 kHz current to a volunteer during the first time period for 7 ms at 200 V base-to-peak, in order to ablate at least a portion of the epidermis, and produce micro-channels. During the second time period, array 44 was maintained at the same place as during the first time period, and applied 100 kHz current for approximately 20 seconds, at 80 V base-to-peak. The volunteer reported no unpleasant sensation due to current application during either period. In other experiments described hereinbelow, similar first-time-period protocols were used, without a second time period, and produced measurable wrinkle reduction. In this first and second time period experiment, no measurements were made of wrinkle reduction.

Heating body fluid 54 within micro-channels 50 leads to the controlled heating of underlying collagen tissue, causing thermally-mediated collagen contraction. Thermally-mediated collagen contraction, or shrinkage, typically results in a tightening effect of the skin. Skin tightening and wrinkle reduction are the synergistic effect of the ablation and lower-temperature heating methods of these embodiments of the present invention.

Typically, the use of apparatus 40 results in skin rejuvenation and wrinkle reduction.

In experiments described hereinbelow, performed by the inventors using a version of apparatus 40 that only ablates and does not utilize heating during the second time period, ablation of micro-channels 50 was found to trigger a wound healing process in the skin, in which collagen formation is naturally induced.

The following examples are provided in order to illustrate the effects of embodiments of the present invention.

Figure 2:
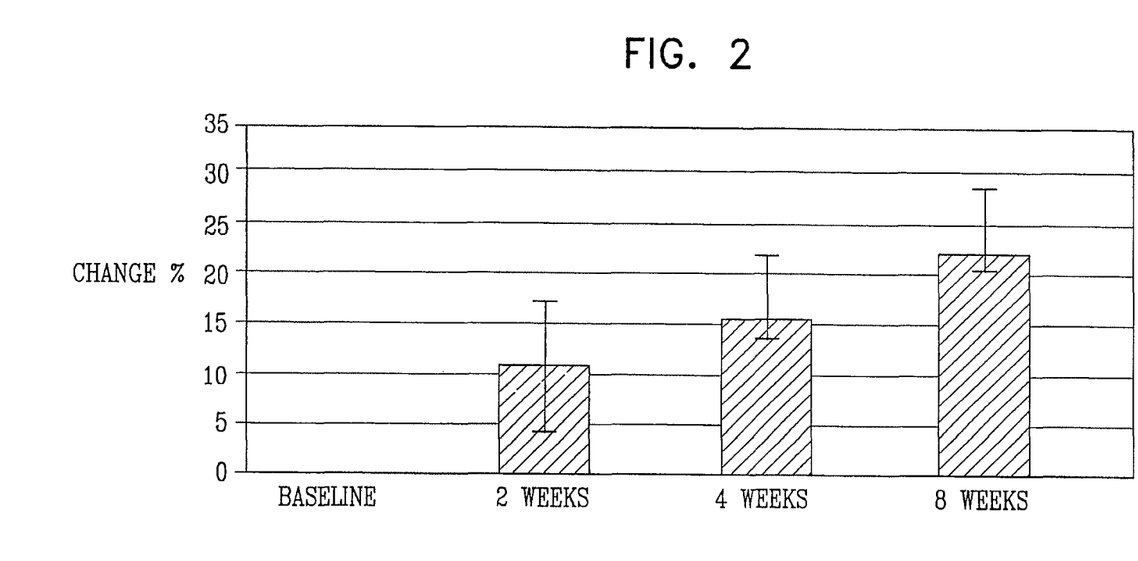
FIG. 2 is a graph representing an average change in wrinkle depth of eight subjects following application of RF energy, in accordance with some applications of the present invention.

FIG. 2 is a graph representing the average changes in wrinkle depth in response to treatment by the method and apparatus for electrical skin rejuvenation, in accordance with some applications of the present invention. In this set of experiments, wrinkle depth on a subject's forehead was determined by silicone imprint analysis of the wrinkles examined. Skin surfaces containing wrinkles from eight subjects were subjected to two treatments with apparatus 40 separated by one month, and measurement were taken prior to the first treatment, and over the course of the next two months. Each treatment comprised applying RF energy through 200 um long electrodes in an array 44 of 144 electrodes, at a voltage of 330 V and a frequency of 100 kHz. The energy was applied to the skin surface in one burst of energy, for a duration of 9 ms. Subsequently, array 44 was removed from the skin and then replaced, within the abilities of the experimenter, on essentially the same location (but not the identical location), such that effectively the same area of skin was covered by the array, even though the electrodes were at an uncontrolled location with respect to the previously-generated micro-channels. Current was applied again, using the same protocol. Subsequently, array 44 was again removed and replaced, and current was applied a third time, again using the same protocol.

As shown in FIG. 2, there is a clear change over time in wrinkle depth in treated skin surfaces over eight weeks. All subjects responded to the treatment and demonstrated gradual improvement and a decrease in wrinkle depth during the course of the study. After two weeks, four weeks and eight weeks the average improvement was 11.06%, 18.25% and 25.3% respectively.

Table I is a table representing skin analysis of eight subjects following treatment by the method and apparatus described herein for electrical skin rejuvenation, in accordance with some applications of the present invention, using the protocol described hereinabove with reference to FIG. 2.

TABLE I

| Group | Subject Number | Subject Age | Epidermis Cell Proliferation Treated | Epidermis Cell Proliferation Non-treated | Collagen Fiber Content | Elastin Fiber Content |
|---|---|---|---|---|---|---|
| A | 1 | 35 | 23 | 19 | no change | no change |
| A | 2 | 40 | 14 | 16 | no change | no change |
| A | 3 | 41 | 31 | 19 | no change | no change |
| A | 4 | 42 | 12 | 30 | no change | increase in fiber content |
| B | 5 | 47 | 60 | 37 | increase in fiber content | increase in fiber content |
| B | 6 | 47 | 25 | 18 | small increase in fiber content | increase in fiber content |
| B | 7 | 50 | 20 | 13 | increase in fiber content | no change |
| B | 8 | 51 | 56 | 16 | increase in fiber content | increase in fiber content |

In this set of experiments, forearm skin biopsy samples were taken from treated and non-treated skin surfaces of eight subjects. The subjects were divided into two age groups. The younger age group (35-42 y) was designated group A, and the older age group (47-51 y) was designated group B. The skin samples were analyzed for collagen and elastin content, as determined by collagen and elastin staining; and epidermal cell proliferation, as determined by a specific marker for proliferating cells (Ki67). As shown in Table I, all subjects in group B showed increased collagen fiber content and increased skin cell proliferation in response to treatment by the method and apparatus for skin rejuvenation, in accordance with some applications of the present invention. Additionally, 75% of the subjects in group B, showed an increase in elastin fiber content. In contrast, the collagen fiber content of subjects in group A was not altered by the treatment. In addition, only 25% of the subjects in group A showed increased elastin content and 50% exhibited increased cell proliferation in response to treatment. Separate results (not shown) demonstrated that pain, erythema, and edema produced during the study were acceptable in each of the test subjects.

Trans Epidermal Water Loss (TEWL) was analyzed following treatment of skin surfaces of foreheads and forearms of subjects. The skin surfaces were treated with the method and apparatus for skin rejuvenation, in accordance with some applications of the present invention. Analysis of the results of the studies preformed on the forearm site show that following the first treatment, TEWL value was significantly higher than the TEWL value measured prior to initiation of treatment (as measured with a VapoMeter (Delfin Technologies, Ltd.) (p=0.012) and according to the Wilcoxon signed-ranks test. TEWL values remained significantly elevated for 48 hours to one week following treatment. (Similar results were obtained for the forehead site.)

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for reducing a wrinkle on a skin surface, comprising:
   identifying a skin surface with a wrinkle;
   positioning at respective sites on the skin surface an array of electrodes communicatively coupled to an energy source; and
   while the electrodes are positioned at the respective sites:
      during a first time period, applying energy from the energy source to drive the electrodes to apply a radio frequency (RF) current at a first voltage sufficient to ablate micro-channels in the epidermal layer of the skin and, at least partially, ablate collagenous dermal tissue, the micro-channels accessing the ablated collagenous dermal tissue; and
      during a second time period, applying energy from the energy source to drive the electrodes to apply a current at a second voltage lower than the first voltage;
   wherein applying energy during the second time period comprises initiating application of the energy:
      at least 10 ms after the first time period application of energy; and
      subsequent to filling of the micro-channels with body fluid.

2. The method according to claim 1, wherein applying energy during the first time period comprises applying the energy for 1-20 ms.

3. The method according to claim 1, wherein applying energy during the second time period comprises applying the energy for at least 1 second.

4. The method according to claim 1, wherein applying energy during the second time period comprises applying only non-ablating energy during the second time period.

5. The method according to claim 1, wherein applying energy during the first time period comprises setting a voltage of the energy applied during the first time period to be 150-350 V base-to-peak.

6. The method according to claim 1, wherein applying energy during the second time period comprises setting a voltage of the energy applied during the second time period to be 10-200 V base-to-peak.

7. The method according to claim 1, wherein applying energy during the second time period comprises setting a voltage of the energy applied during the second time period to be 10-100 V base-to-peak.

8. The method according to claim 1, wherein applying energy during the first time period comprises setting a frequency of the energy applied during the first time period to be 50-500 kHz.

9. The method according to claim 1, wherein applying energy during the second time period comprises setting a frequency of the energy applied during the second time period to be 50-500 kHz.

10. A method for reducing a wrinkle on a skin surface, comprising:
    identifying a skin surface with a wrinkle;
    positioning at respective sites on the skin surface an array of electrodes communicatively coupled to an energy source; and
    while the electrodes are positioned at the respective sites:
       during a first time period, applying energy from the energy source to drive the electrodes to apply a radio frequency (RF) current at a first voltage for 1-20 ms, the first voltage sufficient to ablate micro-channels in the epidermal layer of the skin and, at least partially, ablate collagenous dermal tissue, the micro-channels accessing the ablated collagenous dermal tissue; and during a second time period, applying energy from the energy source to drive the electrodes to apply a current at a second voltage lower than the first voltage for at least 1 second;
wherein applying energy during the second time period comprises initiating application of the energy:
at least 10-99 ms after the first time period application of energy; and
subsequent to filling of the micro-channels with body fluid.

* * * * *